US005474572A

United States Patent [19]

Hayhurst

[11] Patent Number: 5,474,572
[45] Date of Patent: *Dec. 12, 1995

[54] CLIP FOR SUTURE

[76] Inventor: John O. Hayhurst, 14751 SE. Wanda Dr., Milwaukie, Oreg. 97267

[ * ] Notice: The term of this patent shall not extend beyond the expiration date of Pat. No. 5,078,731.

[21] Appl. No.: 207,221

[22] Filed: Mar. 3, 1994

Related U.S. Application Data

[63] Continuation of Ser. No. 1,268, Jan. 7, 1993, abandoned, which is a continuation of PCT/US91/08780, Nov. 22, 1991.

[51] Int. Cl.⁶ ................................................. A61B 17/09
[52] U.S. Cl. ........................... 606/232; 606/151; 606/157
[58] Field of Search .................................. 606/151, 157, 606/158, 232

[56] References Cited

U.S. PATENT DOCUMENTS

| | | | |
|---|---|---|---|
| D. 190,787 | 6/1961 | Schneider | D24/27 |
| D. 234,204 | 1/1978 | Miller et al. | D24/27 |
| 600,887 | 3/1898 | Pettit | 606/120 |
| 3,698,681 | 10/1972 | Lacey | 24/129 R |
| 3,854,482 | 12/1974 | Laugherty et al. | 606/120 |
| 3,874,042 | 4/1975 | Eddleman et al. | 606/157 |
| 3,896,527 | 7/1975 | Miller et al. | 24/499 |
| 3,976,079 | 8/1976 | Samuels et al. | |
| 4,291,698 | 9/1981 | Fuchs et al. | 606/232 |
| 4,382,453 | 5/1983 | Bujan et al. | 606/157 |
| 4,498,476 | 2/1985 | Cerwin et al. | 606/158 |
| 4,519,392 | 5/1985 | Lingua | 606/151 |
| 4,536,924 | 8/1985 | Willoughby | 24/543 |
| 4,620,541 | 11/1986 | Gertzman et al. | |
| 4,623,102 | 11/1986 | Hough, Jr. | 24/543 |
| 4,750,492 | 6/1988 | Jacobs | 606/232 |
| 4,866,818 | 9/1989 | Thompson | 24/543 |
| 5,078,731 | 1/1992 | Hayhurst | 606/232 |
| 5,171,251 | 12/1992 | Bregen et al. | 606/157 |
| 5,234,449 | 8/1993 | Bruker et al. | 606/157 |

FOREIGN PATENT DOCUMENTS 2520606  5/1983  France.

OTHER PUBLICATIONS

Schaefer et al., *Absorbable Ligating Clips,* Surgery, Gynecology & Obstetrics, Apr., 1982, vol. 154, pp. 513–516.

*Primary Examiner*—Gary Jackson
*Attorney, Agent, or Firm*—Klarquist Sparkman Campbell Leigh & Whinston

[57] ABSTRACT

Eliminates the need for tying knots in sutures. The clip (20) is slidable in an open position along sutures (12) that extend from a suturing site. With the clip (20) at the suturing site, the sutures (12) are tensed and the clip is forced into a closed position that fixes the position of the clip (20) relative to the sutures (12).

10 Claims, 3 Drawing Sheets

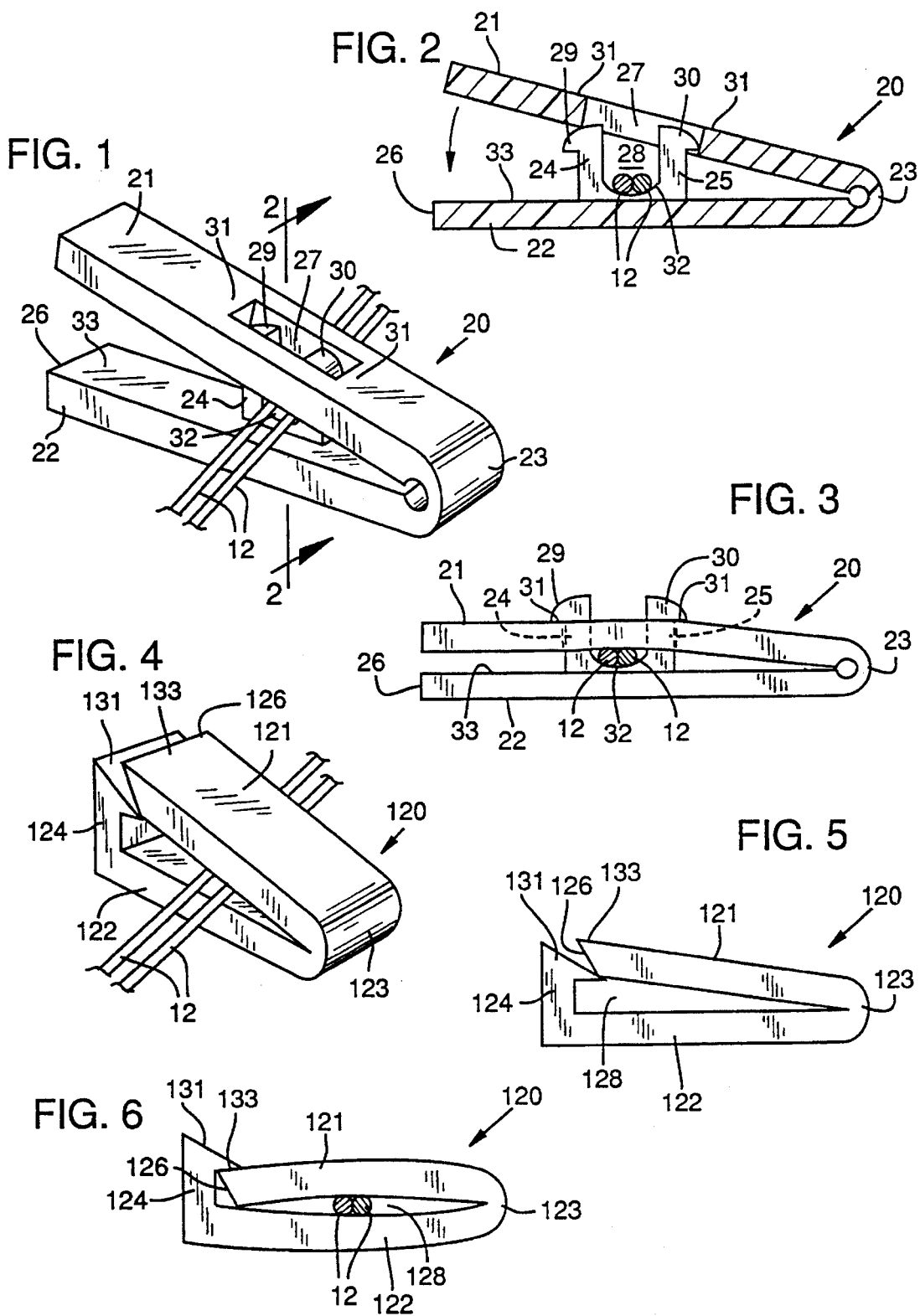

5,474,572

CLIP FOR SUTURE

RELATED APPLICATIONS

This application is a continuation of application Ser. No. 08/001,268, filed on Jan. 7, 1993, now abandoned, which is a continuation in part of International Application No. PCT US91/08,780, filed Nov. 22, 1991, and designating the United States.

TECHNICAL FIELD

This invention relates to clips used in surgical procedures and particularly to clips for securing the free ends of sutures.

BACKGROUND INFORMATION

Sutures are commonly used to close incisions and to reunite damaged tissue. Typically, the sutures are passed through the tissue and the free ends of the sutures are tied together. In many instances, the suturing site is exposed to an extent that is sufficient to permit the surgeon to quickly tie the suture by hand. However, in some procedures, such as arthroscopic surgery, the suturing site is inaccessible by hand. As a result, the surgeon must tie the suture ends into a knot at a location remote from the suture site, and then manipulate suitably configured instruments for sliding the knot to the site.

For example, an arthroscopic surgical procedure usually employs a small-diameter cannula that extends through a small incision made in a joint. The sutures extend from the suturing site through the cannula. The exposed free ends of the sutures are tied by the surgeon and the knot is slid through the cannula to the suturing site. Such a suturing procedure is time consuming and can result in knots that do not hold the suture ends with sufficient tension to securely reunite the tissue.

SUMMARY OF THE INVENTION

This invention relates to a suture clip that eliminates the need for tying knots in suture ends. The clip is slidable along a suture or pair of sutures from a remote location to a suturing site. With the clip at the suturing site, the suture is tensed and the clip is closed against the suture to securely fasten the suture at the site.

The suture clip of the present invention comprises a pair of legs attached together at one end by a hinge. The clip is made of resilient material, such as plastic. The clip is configured so that the elasticity of the plastic biases the legs toward a generally V-shaped orientation that defines the open position of the clip. Prongs are attached to one leg for holding both legs together in a closed position.

The prongs and clip legs define a passageway whenever the clip is in an open position. The free ends of a suture are threaded through the passageway. With the sutures threaded through the passageway, the open suture clip may be slid along the sutures without passing laterally away from the sutures because the passageway surrounds the sutures. The clip is slid down the sutures and passed through the arthroscopic incision until it reaches a position adjacent to the tissue where the suture is to be secured. An appropriate surgical instrument is used for sliding the clip along the sutures and for closing the clip. When the clip is forced into the closed position, the legs pinch the sutures to fasten the clip and sutures together. In one embodiment, the sutures are captured between the legs of the clip in a serpentine path, thereby increasing the resistance to slippage of the clip along the sutures.

BRIEF DESCRIPTION OF THE DRAWINGS

FIG. 1 is a perspective view of one embodiment of a suture clip of the present invention, showing the clip in an open position.

FIG. 2 is a cross-sectional side view, taken along line 2—2 of FIG. 1, showing sutures passing through the open clip.

FIG. 3 is a side view of the clip of FIG. 1, showing the clip in a closed position with sutures pinched between the legs of the clip.

FIG. 4 is a perspective view of another embodiment of the present invention, showing the clip in an open position.

FIG. 5 is a side view of the suture clip of FIG. 4.

FIG. 6 is a side view of the suture clip of FIG. 4, showing the clip in a closed position with sutures pinched between the legs of the clip.

DESCRIPTION OF THE PREFERRED EMBODIMENTS

Figure 7:
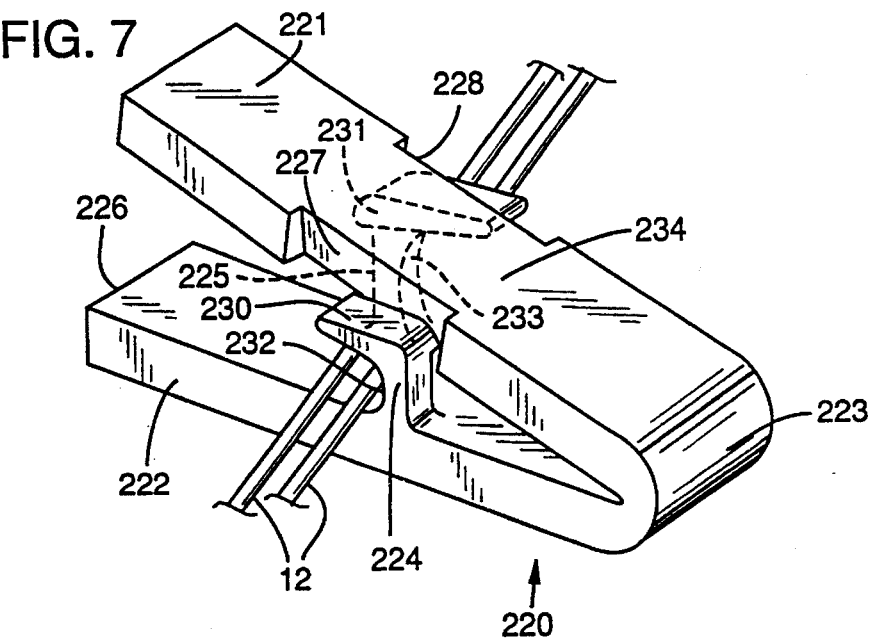
FIG. 7 is a perspective view of another embodiment of the present invention, showing the clip in an open position.
Figure 8:
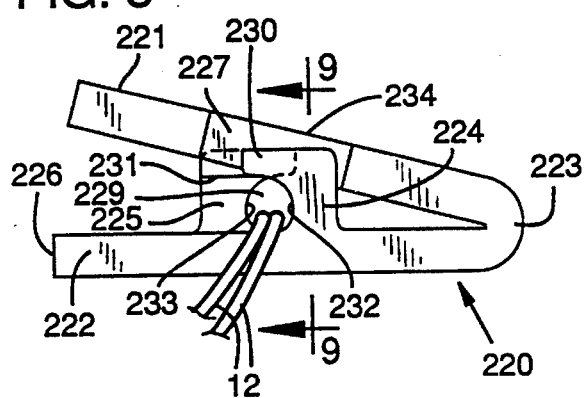
FIG. 8 is a side view of the embodiment of FIG. 7.
Figure 9:
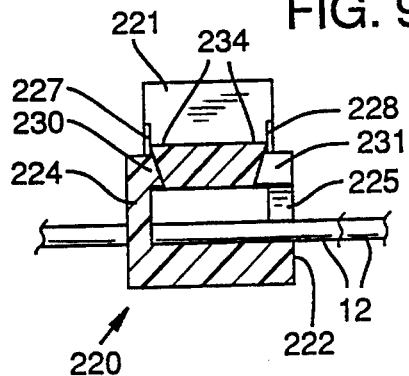
FIG. 9 is a cross-sectional view, taken along line 9—9 of FIG. 8.

FIGS. 1, 2 and 3 show one embodiment of a suture clip 20 formed in accordance with the present invention. The suture clip 20 includes an upper leg 21 and a lower leg 22, joined at a flexible hinge 23. The legs 21, 22 move about the hinge 23 between an open position (FIG. 1) and a closed position (FIG. 3). The clip 20 is formed of resilient material that normally biases the clip toward the open position, wherein the legs 21, 22 assume a V-shaped orientation.

A first prong 24 and a second prong 25 are attached to the lower leg 22 and extend toward the upper leg 21. The prongs 24, 25 are attached between the hinge 23 and the free end 26 of the lower leg 22.

The upper leg 21 has an opening 27 that is located to receive the prongs 24 and 25 whenever the clip 20 is moved to the closed position, as described more fully below. Whenever the clip is in the open position, the prongs 24, 25 extend partly into the opening 27 (FIG. 2). A passageway 28 is defined between the first prong 24 and second prong 25, and between the lower leg 22 and the upper leg 21. The passageway 28 has no lateral opening. Consequently, one or more sutures 12 may be threaded through the passageway 28, and the open clip 20 may be slid along the length of the sutures 12 without moving laterally away from the sutures.

For example, an open clip 20 may be slid along the sutures that extend from a suturing site that is located inside a joint that is accessible only by surgical instruments. As used herein, the term suturing site means the location adjacent to the tissue to which the suture is connected. The free ends of the sutures 12 that are exposed outside of the joint are threaded through the passageway 28 of the clip, and the clip is slid down the sutures 12. The clip 20 will remain in contact with the sutures as it is slid to the suturing site because, as noted earlier, the passageway 28 in the open clip 20 has no lateral opening. In this regard, the sutures act as a guide for moving the clip to the suturing site. Once in position at the suturing site, the suture is tensed and the clip is closed (FIG. 3) by an appropriate surgical instrument, such as a clamp.

The prongs 24, 25 serve to lock the clip 20 in a closed position. To this end, a hook 29 is formed on the end of the first prong 24 and a correspondingly shaped hook 30 is formed on the second prong 25. The hooks 29 and 30 extend apart a distance that is greater than the length of the opening 27 in the upper leg 21. Consequently, as the upper leg 21 is forced toward the lower leg 22, the first prong 24 and second prong 25 are deflected toward one another as the opening 27 is slid over the curved tops of the hooks. Once the hooks 29 and 30 extend through the opening 27, the prongs 24 and 25 snap apart so that the hooks 29 and 30 extend partly over the outer surface 31 of leg 21 near the opening 27, thereby locking the clip 20 in the closed position. With the clip locked in the closed position, the sutures 12 are firmly pinched between the legs 21, 22 (FIG. 3) so that the clip is unable to slide along the sutures 12.

As best shown in FIG. 2, a curved platform 32 is formed between the prongs 24, 25. The platform 32 provides a surface that is raised slightly above the inner surface 33 of the lower leg 22. The platform 32 effectively carries the sutures 12 above the inner surface 33 of the lower leg 21 to ensure the sutures 12 will be tightly pinched between the legs 21, 22 when the clip is closed.

The clip 20 is of unitary construction and is preferably made of plastic. The plastic material provides the resiliency for urging the clip 20 into the open position and for permitting deflection of the prongs 24, 25 as described above. Preferably, the clip 20 is made of material that is gradually absorbed. Such materials are polyglycolic acid, polyactic acid and trimethylene carbonate copolymers. Alternatively, the clip may be formed of permanent or non-absorbable materials, such a acetal homopolymers or copolymers, polyethylene, polyproplylene, and copolymers thereof.

FIGS. 4, 5, and 6 show another embodiment of the invention wherein the passageway 128 of the clip 120 is defined by a single prong 124 attached to the end of the lower leg 122. The hinge 123 biases the clip 120 into a V-shaped open position (FIG. 5).

In the embodiment of FIG. 4, the single prong 124 is attached to the distal end of lower leg 122 and extends toward the upper leg 121. When the clip is in the open position, the prong 124 is in contact with the free end 126 of upper leg 121, thereby forming a passageway 128 surrounded by the prong 124, the lower leg 122, and the upper leg 121. The passageway 128 has no lateral opening. Any sutures 12 that are threaded through the passageway 128 are, therefore, substantially surrounded. As a result, the open clip 120 may be slid along the sutures 12 without moving laterally away from the sutures.

The prong 124 serves to lock the clip 120 in a closed position. A hook 131 is formed on the end of the prong 124. As the upper leg 121 is forced toward the lower leg 122, the prong 124 is deflected away from the upper leg 121 as the free end 126 of the upper leg 121 slides over the angled top of the hook. Once the hook 131 extends over the upper surface 133 of upper leg 121, the prong snaps back so that the hook 124 extends partly over the upper surface 133 of leg 121 near the free end 126, thereby locking the clip 120 in the closed position. When the clip is locked in the closed position, the sutures 12 are firmly pinched between the legs 121, 122.

FIGS. 7–11 show another embodiment of the suture clip 220 of the present invention. This embodiment includes an upper leg 221 and a lower leg 222, connected together at a flexible hinge 223. As with the other embodiments, this clip is formed of a resilient material that biases the clip toward the open position, wherein the legs 221, 222 assume a V-shaped orientation.

A first prong 224 and a second prong 225 are attached to the lower leg 222 and extend toward the upper leg 221. The prongs 224, 225 are attached between the hinge 223 and the free end 226 of lower leg 222. Each prong 224, 255 includes an inwardly protruding hook 230, 231.

Figure 10:
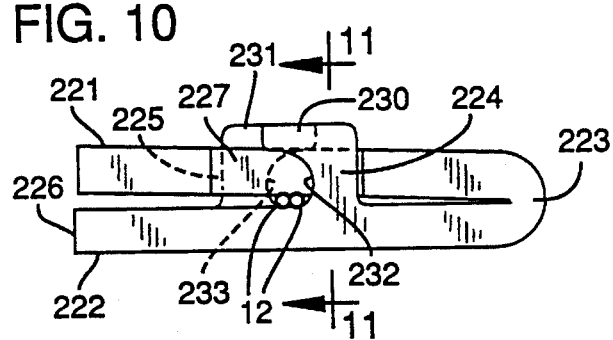
FIG. 10 is a side view of the embodiment of FIG. 7, showing the clip in a closed position with sutures pinched between the legs of the clip.
Figure 11:
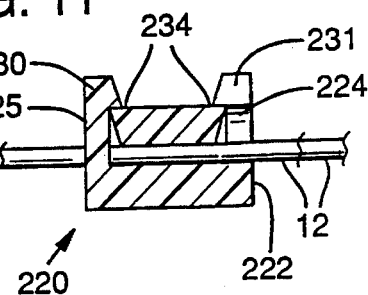
FIG. 11 is a cross-sectional view, taken along line 11—11 of FIG. 10.

The upper leg 221 has a first notch 227 located to receive the prong 224, and a second notch 228 located to receive prong 225 when the clip is forced into the closed and locked position (FIG. 10). When the clip 220 is in the open position (FIG. 8), the hook 230 on prong 224 contacts the leg 221 at one notch 227, and the hook 231 on prong 225 contacts the leg 221 at the other notch 228.

A passageway 229 is defined between the first prong 224 and the second prong 225, and between the lower leg 222 and the upper leg 221. One side 232 of the first prong 224 and the corresponding side 233 of the second prong 225 are curved such that the passageway 229 is essentially circular (FIG. 8) when the clip is in the open position. The passageway 229 has no lateral opening and, as with the other embodiments, the open clip 220 may be slid along the sutures 12 without laterally moving away from them.

With the sutures 12 threaded through the passageway 229, and the clip 220 adjacent to the suturing site, the clip 220 is locked in the closed position. In this regard, the hooks 230, 231 formed on the end of the first and second prongs 224, 225 have inclined facing surfaces that permit the upper leg 221 to be forced between the prongs 224, 225 as the clip 220 is moved into the closed position. As the upper leg 221 is forced toward the lower leg 222, the first prong 224 and second prong 225 are deflected away from one another as the portions of the upper leg 221 within the notches 227 and 228 push against the inclined surfaces of the hooks 230, 231. Once the hooks 230, 231 extend past the notches 227 and 228, the prongs 224 and 225 snap together so that the hooks 230, 231 extend partly over the top surface 234 of upper leg 221, thereby locking the clip 220 in the closed position. With the clip locked in the closed position, the sutures 12 are firmly pinched between the legs 221, 222 (FIG. 10) so that the clip is unable to slide along the sutures 12.

Figure 12:
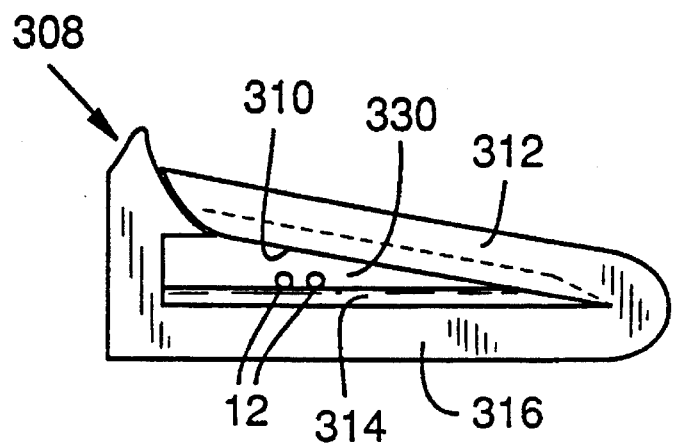
FIG. 12 is a side view of another embodiment of the present invention, showing the clip in an open position.
Figure 13:
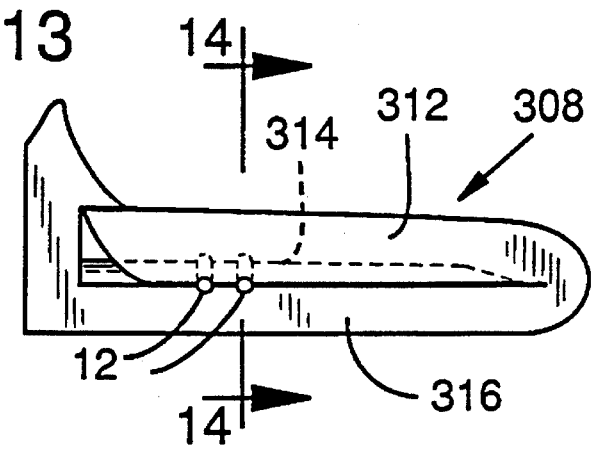
FIG. 13 is a side view of the embodiment of FIG. 12, showing the clip in the closed position.
Figure 14:
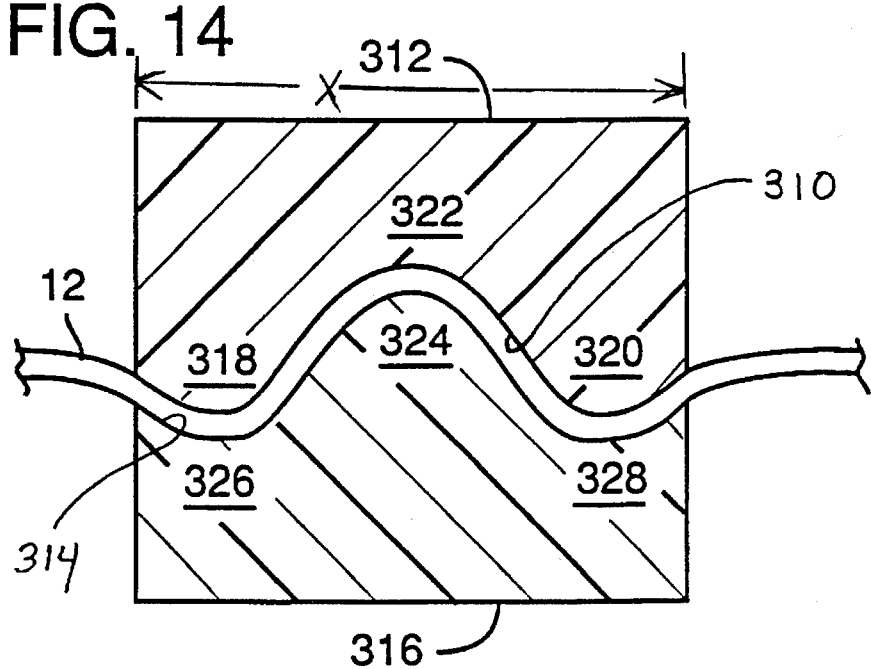
FIG. 14 is a cross-sectional view, taken along line 14—14 of FIG. 13.

Another embodiment of the present invention is shown in FIGS. 12–14. In this embodiment the legs of the clip in the closed position capture the sutures in a serpentine path that is transverse to the longitudinal axis of the legs, thereby increasing the resistance to slippage of the clip along the suture, and providing a more positive connection between the clip and the sutures. The configuration of this embodiment also decreases the possibility of misalignment of the legs when the clip is moved into the closed position.

The clip 308 includes an upper leg 312 that has an inner surface 310 that defines a serpentine shape in cross-section (FIG. 14). The inner surface 314 of lower leg 316 is configured with a complementary serpentine cross-sectional shape.

As shown in FIGS. 12 and 14, the surface 310 of upper leg 312 is defined by two downwardly projecting, generally convex (in cross-section) ridge portions 318 and 320, which are separated by a generally concave valley portion 322. The surface 314 of lower leg 316 is defined by an upwardly projecting, generally convex ridge portion 324 that separates two adjacent concave valley portions 326 and 328.

With clip 308 in the open position (FIG. 12), a passageway 330 is defined, having no lateral opening. Consequently, one or more sutures 12 may be threaded through passageway 330, and the open clip 308 may be slid along the length of the suture without moving laterally away from the suture.

Once the clip is moved adjacent the suturing site, it is locked into the closed position (FIG. 13) in the manner detailed above. In the closed position, the ridge portions and the valley on upper leg 312 mate with the valley portions and the ridge on lower leg 316, as illustrated, to define a transverse serpentine path along which pass the sutures that are threaded through the clip. In this position, the sutures contact surface 310 of upper leg 312 and surface 314 of lower leg 316, along the entire length of the path.

Because the sutures follow a serpentine path, the contact length between sutures 12 and clip 308 is substantially greater than the length of contact between the generally flat inner surfaces of the legs illustrated in the embodiment shown in FIG. 4. Put another way, the length of the path (FIG. 14) and, therefore, the length of contact between the sutures and the legs, is greater than the width of the legs in the direction transverse to the longitudinal axis of the legs (distance "X" in FIG. 14). Accordingly, the curves in the path increase the length of the sutures that is compressed between the legs of the closed clip. The increased contact length between the suture and the legs increases the resistance of clip 308 to sliding laterally along the sutures as a result of the increased frictional resistance between the sutures and the legs.

The serpentine or curved path for capturing the suture also has the effect of increasing frictional resistance to suture slipping when the suture is tensed. More particularly, tension imparted in the sutures (which tension would arise, for example, in instances where the clip is sited firmly against tissue with the suture held taut as the clip is closed) will, throughout most of the length of the serpentine path, transfer a component of that tension force in a direction normal to the leg surfaces 310, 314, thereby supplementing the frictional resistance attributable to the sutures being compressed within the elongated serpentine path.

In the preferred embodiment, the legs are formed to define a very narrow gap between the upper surface 310 and lower surface 314 when the clip is closed. To this end, the clip is formed with the cross-sectional width of the ridge portions 318, 320 and 324 being slightly narrower than the cross-sectional width of the complementary valley portions 326, 328 and 322. The gap, which is formed to be less than the width of the sutures, reduces the shear stress on the captured suture, thereby reducing the possibility of breaking the suture. This configuration also reduces the amount to which the sutures are stretched over the serpentine portions of the legs when the clip is closed, to further decrease the possibility of breaking the suture.

Neither the number of ridges and valleys on the upper and lower legs, nor the respective height of the ridges and valleys is critical. Thus, the clip may be formed with greater or fewer ridges and valleys than are illustrated in FIGS. 12–14, and the size of the ridges and valleys may be varied. The position of the ridges and valleys relative to one another on the legs, and the cross-sectional shape of the ridges and valleys is also not critical.

Other complementary mating configurations between the upper and lower legs will also suffice to increase the length of contact and the forces between the sutures and the clip, thereby increasing frictional resistance. Alternatively, frictional resistance between the sutures and the clip may be increased by roughening the mating surfaces of the legs. For example, with any of the embodiments illustrated, the resilient material used to form the clip may be unpolished on the inner surfaces of the legs. The surfaces also may be deliberately roughened after the clip is molded.

While the present invention has been described in accordance with several embodiments, it is recognized that variations and changes may be made therein without departing from the scope of the invention as set forth in the claims.

I claim:

1. A clip for securing a suture comprising:

a first leg;

a second leg attached to the first leg, the first and second leg being movable relative to one another; and the clip being constructed of a resilient material that normally urges the first and second legs toward a first position that defines a passageway that is circumscribed by the clip when the legs are in the first position; and an elongate suture threaded through the passageway, the suture being completely surrounded by the clip when the legs are in the first position, the first and second legs being movable from the first position to a closed position for preventing movement of the clip relative to the suture threaded through the passageway, the clip in the closed position defining a curved path along which the suture may be positioned to be held between the legs.

2. The clip according to claim 1, wherein the closed clip has a width through which the suture passes and wherein the curved path length is greater than the width.

3. The clip according to claim 1, wherein the length of the curved path is greater than the transverse width of either of the legs.

4. The clip of claim 1 wherein part of the curved path is roughened.

5. A one-piece suture clip made from a resilient material and adapted for clipping to a suture and comprising:

a first and second leg attached to one another by a hinge and movable relative to each other between an open position and a closed position, the first leg having a first inner surface defining a serpentine shape and the second leg having a second inner surface defining a serpentine shape that conforms to the serpentine shape of the first inner surface;

a prong attached to the first leg, the prong and the legs defining a passageway that is substantially surrounded by the legs and the prong when the legs are in the open position, the first and second legs defining a serpentine path therebetween when the legs are in the closed position.

6. The suture clip according to claim 5, wherein each leg has a transverse width and the serpentine path has a length that is greater than the transverse width of either of the legs.

7. The suture clip according to claim 5, wherein a suture is disposed between the legs so that the inner surfaces of the legs are in contact with the suture along the entire length of the serpentine path when the legs are in the closed position.

8. A method for fastening a suture near a suturing site, comprising the steps:

providing a suture connected at a suturing site and having a free end;

providing a clip having a first leg and a second leg hinged to the first leg, the legs being movable between an open position and a closed position and made of a resilient material to bias the legs to the open position so that a passageway is defined therebetween;

threading the free end through the passageway, the clip completely surrounding the threaded suture when the legs are in the open position;

sliding the clip along the suture to a position adjacent to the suturing site; and moving the legs from the open position to the closed position so that the suture is secured to the clip.

9. The method of claim 8 wherein each leg of said clip is provided with s curved inner surface, the surfaces facing one another to form a curved path therebetween when the legs are in the closed position.

10. The method of claim 8 further including the step of applying a pressure to the entire length of the suture held between the legs.

* * * * *